(12) United States Patent
Mainelis

(10) Patent No.: US 8,186,235 B2
(45) Date of Patent: May 29, 2012

(54) METHOD AND DEVICE FOR THE COLLECTION OF AIRBORNE PARTICLES AND THEIR CONCENTRATION IN SMALL AMOUNTS OF LIQUID

(76) Inventor: Gediminas Mainelis, Milltown, NJ (US)

( * ) Notice: Subject to any disclaimer, the term of this patent is extended or adjusted under 35 U.S.C. 154(b) by 392 days.

(21) Appl. No.: 12/490,011

(22) Filed: Jun. 23, 2009

(65) Prior Publication Data

US 2009/0320618 A1    Dec. 31, 2009

Related U.S. Application Data

(60) Provisional application No. 61/133,451, filed on Jun. 30, 2008.

(51) Int. Cl.
 *G01N 1/04*   (2006.01)
(52) U.S. Cl. .................................................. 73/864.71
(58) Field of Classification Search ........ 73/843–864.91
 See application file for complete search history.

(56) References Cited

U.S. PATENT DOCUMENTS

2010/0062415 A1*  3/2010  Schwoebel et al. ............... 435/5
2010/0186524 A1*  7/2010  Ariessohn et al. ......... 73/863.22

\* cited by examiner

*Primary Examiner* — Hezron E Williams
*Assistant Examiner* — Jamar Ray
(74) *Attorney, Agent, or Firm* — Fox Rothschild LLP

(57) ABSTRACT

A method and its possible embodiments are presented for collecting airborne biological and non-biological agents and concentrating them into small amounts of liquid. Airborne particles are drawn into the sampler and by the action of an electrostatic field are deposited on the collection electrode covered with superhydrophobic substance (surface contact angle >150°). At the end of the sampling period a small liquid droplet (5-60 μL) is injected at the top of the sampling chamber. Since the sampler is positioned at an angle to the horizontal, the droplet rolls-off of collection electrode's surface under the force of gravity and removes the deposited particles. The droplet is then collected by a liquid capture system. The particles concentrated in such small amounts of liquid facilitate sample analysis by various techniques. The suggested sampler's embodiments achieve sample concentration rates higher than $1 \times 10^6$/min which will allow detection of very low particle concentrations.

8 Claims, 10 Drawing Sheets

Figure 1A:
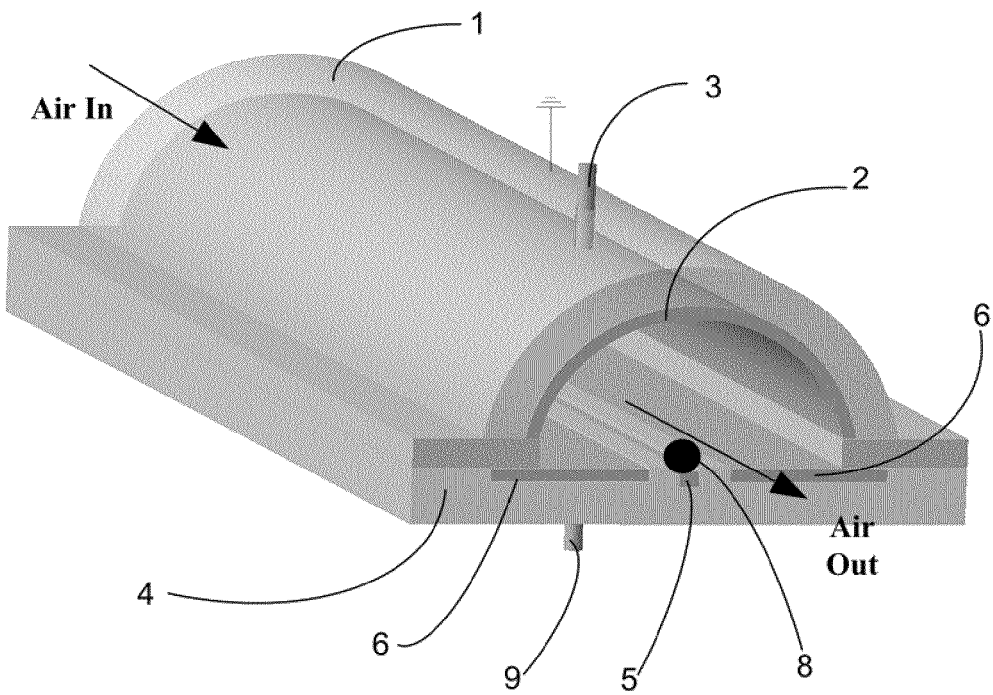

METHOD AND DEVICE FOR THE COLLECTION OF AIRBORNE PARTICLES AND THEIR CONCENTRATION IN SMALL AMOUNTS OF LIQUID

CROSS-REFERENCE TO RELATED PUBLICATIONS

Provisional application 61/133,451 filed on Jun. 30, 2008.

FEDERALLY SPONSORED RESEARCH OR DEVELOPMENT

The proposed sampling method's reduction to practice was supported by the National Institute for Occupational Safety and Health, under the grant R21OH008656.

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention is directed to a method and device for collection of airborne particles and their concentration in very small amounts of liquid (μL) for further analysis and investigation. The method can be applied for the sampling and/or collection of airborne particles of non-biological as well as of biological origin, such as bacteria, fungi and their mixtures. Ability of the proposed method to concentrate the collected biological airborne particles into extremely small amounts of liquid increases sensitivity of this method and device and makes them especially applicable for biodefense purposes.

2. Description of Related Art

Exposure to airborne biological agents, especially pathogenic or allergenic microorganisms, may cause a wide range of respiratory and other health disorders in occupational and general populations. Moreover, health-care professionals increasingly recognize bioaerosols as a cause of preventable airborne infections and hypersensitivity diseases (WHO, 1990). Although relatively little data exist on the presence of cells or cell material of fungi and bacteria in fine particle samples (Womiloju et al., 2003), some studies indicate that perhaps as many as 10% of urban and rural fine aerosols are biological in nature (Monn, 2001), which stresses the need to develop advanced tools needed to assess and control our exposure to airborne microorganisms (bioaerosols) indoors and outdoors, and to protect the populations and resources potentially exposed to airborne microbial agents. It has been concluded that many bioaerosol species that may cause health effects are currently not yet identified and more research is needed to establish better tools for assessing exposure to biological aerosols (Douwes et al., 2003). In addition, improved exposure assessment and protection of populations and resources at risk from biowarfare agents requires advanced air sampling devices that feature high collection efficiency and can detect low agent concentrations.

Currently, bioaerosols are commonly collected using techniques that require active sampling, such as impaction, impingement or deposition on filters. Recently, there has been an increased interest in collection of microorganisms using electrostatic precipitation due to its lower power requirements compared to inertial techniques while still allowing efficient particle removal from the air. In electrostatic precipitators, airborne particles are electrically charged and then removed from the air stream by electrostatic field. Removal of non-biological aerosol particles by electrostatic precipitators has been widely studied from the theoretical and practical points of view (Rose and Wood, 1956; Lu and Hungsung, 1998; Zhuang et al., 2000), owing to its widespread practical applications. These devices provide efficient particle capture while causing minimal impedance to the gas flow.

An investigation and a successful practical application of electrostatic precipitation for collection and enumeration of viable airborne microorganisms have also been described. The studies showed that aerosolized *Pseudomonas fluorescens* bacteria can carry up to 13,000 elementary charges (Mainelis, 2001) and that they can be effectively collected by an electrostatic technique (Mainelis et al., 2002a; Mainelis et al., 2002c). It was also found that electrostatic fields are unlikely to damage the organisms passing through an electrostatic collector or those microorganisms already deposited on an agar medium (Yao et al., 2005). Based on these observations, an electrostatic precipitator that utilizes natural microorganism charge for their collection was developed and tested (Yao and Mainelis, 2006b). Investigations in indoor and outdoor environments of said sampler showed that it recovered from 5 to 10 times higher concentrations of culturable microorganisms compared to a traditional impactor.

A method used to analyze biological and non-biological particles collected by various samplers depends on the sampling medium. Liquid is often a preferred sampling medium because of its versatility. Biological particles in liquid samples can be analyzed by numerous techniques, including, but not limited to, microscopy, culturing techniques, and various microbiological techniques, such as polymerase chain reaction (PCR), enzyme-linked immuno assays (ELISA) and similar. Performance of a liquid-based aerosol collector to detect the presence of airborne particles is determined not only by its collection efficiency, but also by its concentration rate. High concentration rates reduce the sampling time needed to detect airborne particles and enable detection of lower particle concentrations (Haglund, 2003). The concentration rate is defined as the rate with which particles present in an air volume are concentrated in a liquid volume per time period:

$$\text{Concentration rate, } R_C \ (t^{-1}) = \frac{\text{Airborne particle concentration } (L^{-1})}{\text{Particle concentration in liquid } (L^{-1})} \quad (1)$$

$$= \frac{Q(L/\min)}{v(L)} \eta,$$

where Q is the sampling flow rate, v is the sample volume and η-collection efficiency. Traditional liquid samplers operate at flow rates up to 20 L/min and feature low sample concentration rates, e.g. up to 2,500 for BioSampler (SKC, Inc., Eighty Four, Pa.) operating at 12.5 L/min and sampling into 5 mL of liquid. Since the anthrax attacks of 2001, several new samplers have been developed for collecting airborne particles into liquid. Among those, InnovaTek, Inc. (Richland, Wash.) introduced the BioGuardian Air Sampler which operates from 100 to 1000 L/min and collects sample into 10-15 mL of liquid. The SpinCon air sampler by Evogen, Inc. (Kansas City, Mo.) samples at 450 L/min and concentrates sample into 10 mL of liquid. The BioCapture 650 (MesoSystems Technology, Inc., Albuquerque, N. Mex.) is a portable sampler that achieves a sampling flow rate of 200 L/min and collects particles into 2-5 mL of liquid. The concentration rates for these samplers are in the order of tens of thousands. A new wetted-wall bioaerosol cyclone developed at the Texas A&M University has concentration rates of approximately $5 \times 10^4$/min for bacteria-sized particles (Seo, 2007). The Lawrence Livermore National Laboratory (Livermore, Calif.) has developed a stationary Autonomous Pathogen Detection System (APDS) that combines a virtual impactor and a wetted-wall cyclone and is capable of continuous and fully autonomous monitoring for multiple biowarfare organisms (McBride et al., 2003; Hindson et al., 2004; Hindson et al., 2005a; Hindson et al., 2005b). The APDS operates at collection flow rates up to 3750 L/min and can achieve concentration rates as high as $7.5 \times 10^5$/min when collecting 3 tan polystyrene latex (PSL) particles into 4 mL of liquid (Mainelis et al., 2005). However, the size of the system, its power and cost requirements are not conducive for its mass deployment.

Given the low power consumption of electrostatic precipitators, several models have been developed to collect particles into liquid. Particles collected electrostatically into liquid can be easily transferred into various analytical devices, such as "laboratories-on-a-chip" which is especially advantageous for the detection and identification of biological agents. U.S. Pat. No. 6,955,075 describes a briefcase-sized electrostatic precipitator that samples at air flow rate of 300 L/min (Carlson, 2005). The particles are electrically charged, deposited onto a vertically tubular collection electrode and continuously washed-off by recirculating liquid. The amount of liquid is not specified, although a presentation by the same authors indicated 20 mL (Carlson, 2004). The U.S. Pat. No. 7,428,848 describes a high throughput electrostatic collector (Pant et al., 2008) where particles are deposited onto a horizontally-oriented collection electrode and are washed off into liquid. One particular embodiment collects particles at a flow rate of 60 L/min into 10 mL of liquid. These samplers mentioned above have maximum concentration rates of about 6,000-15,000/min. Another wet electrostatic collector is described in the U.S. patent application Ser. No. 11/473,748 (Zaromb and Martell, 2007). The device achieves collection efficiency of 94% when collecting 1 μm PSL beads at a flow rate of 510 L/min. The particles collected on the tubular collection electrode are washed of with 3-10 mL of liquid injected at intervals of 5-20 seconds. In one of the described experiments, particles were accumulated in 60 mL of liquid.

Thus, the concentration rates of majority of aerosol/bioaerosol samplers, especially the compact ones, are still in the order of tens of thousands even when assuming 100% collection efficiency. Since the increase in a sampler's concentration rate improves its capabilities to detect a particular biological agent or a pollutant it is important to develop samplers that feature high concentration rates. Compared to inertia-based techniques, electrostatic precipitators require less energy, and thus development of electrostatic samplers capable of high concentration rates is especially beneficial. As could be seen from Eq. 1, the concentration rate could be improved either by increasing the sampling flow rate or by decreasing the sample volume. The electrostatic collectors described in prior art feature sample volumes from 10 to 60 mL (milliliters). In this patent application a method and a device are presented where the sample volume is reduced by three orders (1000×) of magnitude, i.e., to 5-60 μL (microliter). This reduction is critical because modern sample analysis tools use only a fraction of the sample (microliter amounts) for the actual analysis of the sample (Hindson et al., 2005a) and thus the entire sample could be analyzed thus increasing sensitivity of detection.

In this application I present a method and a device, where a combination of electrostatic collection mechanism and a collection surface coated with superhydrophobic material (water contact angle >150°) allows effective collection of particles and, more importantly, allows achieving very high concentration rates. The principle of the method and its ability to achieve concentration rates exceeding $1 \times 10^6$/min distinguish this method and device from prior art.

In nature, superhydrophobic surface properties allow for certain plants ("Lotus leaf" type) to be cleaned from dust pollution by a simple rain shower (Barthlott and Neinhuis, 1997). Superhydrophobic nature (high contact angle) of the leaf's surface makes water droplets form spheres with very little adhesion to the surface and the droplets roll off very easily even at small inclinations under the force of gravity. Microscopic examination of such surfaces revealed the presence of micro-structured surface as well as coating by water-repellent crystals (Ma and Hill, 2006). When a water droplet rolls over a particle deposited on such a surface, the particle is wetted, adheres to the droplet and is removed from the surface. Thus, this "self-cleaning" property of superhydrophobic surface is combined with electrostatic collection mechanism into a new method and a device. Here, the airborne particles are electrostatically deposited onto a superhydrophobic surface from where they are removed and collected by small rolling water droplets (from 5 to 60 μL) for subsequent analysis. In this Electrostatic Precipitator with Superhydrophobic Surface (EPSS) the airborne particles are collected for a desired period of time and the deposited particles are then removed at the end of the sampling period by one small liquid droplet thus accruing all the collected particles in one droplet. Since the deposit is suspended in liquid, the presence of biological/non-biological particles or chemical substances in the sample can be determined by multiple analytical techniques. For biological particles this includes, but is not limited to, the traditional culturing and microscopy techniques as well as the modern molecular analysis tools, such as PCR or ELISA.

BRIEF SUMMARY OF THE INVENTION

A method and its possible embodiments are presented for detecting the presence of airborne biological and non-biological particles. The device is an electrostatic collector, where a combination of electrostatic collection mechanism with superhydrophobic collection surface (surface contact angle >150°) allows for efficient particle collection, removal and concentration in water droplets as small as 5-60 μL. The device comprises two electrodes, one of which is grounded while the other is connected to high voltage having a sign opposite to the sign of electrical charge on the incoming particles. The electrode that is connected to a ground is also called ground electrode. The electrode connected to high voltage is covered by a superhydrophobic substance. The electrode covered by a superhydrophobic substance is also called the collection electrode. The width of this electrode should be similar to the diameter of a droplet used to collect the deposited particles. If the voltage connections are reversed (the electrode with superhydrophobic surface is grounded and the other is connected to high voltage, then the high voltage sign should be the same as the sign of electrical charge on the incoming particles. The electrical charge to the particles is provided by a separate ionizing/charging module positioned in front of the collector. The sampler is positioned at a ~10 degree inclination angle to the horizontal and the charged airborne particles are drawn into the sampler by a pump or an air mover. Once drawn into the sampler, the particles are deposited onto the collection electrode with superhydrophobic surface by the action of electrostatic field. At the end of the sampling period a small water droplet (5-60

μL) is injected at the top of the sampling chamber onto the collection electrode and the droplet rolls-off of electrode's surface under the force of gravity capturing the deposited particles. The droplet can then be analyzed by a variety of techniques. The suggested embodiments of the sampler achieved concentration rate exceeding $1 \times 10^6$/min when sampling biological and non-biological test particles which is much higher than those achieved by prior art. The concentration rate can be improved even further at sampling flow rates of 100 L/min and higher. The ability of the new method to concentrate airborne particles in such small amounts of liquid substantially improves our ability to detect low airborne particle concentrations, including the presence of biothreat agents. Low power and small footprint of the device make it suitable for mass deployment and for biodefense purposes.

BRIEF DESCRIPTION OF THE SEVERAL VIEWS OF THE DRAWING

To facilitate the understanding, identical reference numerals have been used to designate identical elements that are common to the figures.

FIG. 1A depicts overall view of the electrostatic precipitator with superhydrophobic surface (EPSS).

FIG. 1B schematically depicts the bottom plate of the electrostatic precipitator with superhydrophobic surface (EPSS) in more detail and illustrates the initial position of the collecting droplet and the position of liquid capture system.

FIG. 1C schematically illustrates the front view of the electrostatic precipitator with superhydrophobic surface (EPSS) in more detail.

FIG. 1D shows the side view of the electrostatic precipitator with superhydrophobic surface (EPSS) and indicates one possible embodiment of the support system to keep the EPSS inclined at an angle θ to the horizontal.

FIG. 2 schematically shows a different embodiment of electrostatic precipitator with superhydrophobic surface (EPSS) having a shape similar to an inverted triangle.

FIG. 3 shows schematic of the entire sampling system and its components.

FIG. 4 shows experimental setup used to experimentally verify performance of the electrostatic precipitator with superhydrophobic surface (EPSS).

FIG. 5 shows efficiency of particle removal from the EPSS' collection electrode for three sequential 40 µL water droplets as a function of the sampler's inclination angle (1, 5, 10, 20, and 30 degrees) at 10 L/min sampling flow rate and at the 12 V/50 mA charging condition and 7 kV collection voltage. The data are averages and standard deviations from 3 repeats.

FIG. 6 presents sample concentration rates of the EPSS based on the 1$^{st}$ water droplet at two different collection electrode widths (3.2 versus 2.1 mm) and as a function of droplet size (5, 10, 20, 40, and 60 µL) at 10 L/min sampling flow rate and at the 12 V/50 mA charging condition and 7 kV collection voltage with 3.2 µm PSL. The data are averages and standard deviations from 3 repeats.

FIG. 7 shows comparison of concentration rates of the EPSS based on the 1$^{st}$ water droplet for *Pseudomonas fluorescens* and *Bacillus subtilis* bacteria when sampled with 5 µL water droplet at different sampling flow rates and at the 12 V/50 mA charging condition and 7 kV collection voltage. The samples were analyzed using microscopy. The data are averages and standard deviations from 3 repeats.

FIG. 8 shows collection efficiency and concentration rate of the EPSS when the collected bacteria were analyzed using the whole-cell QPCR method. The sampling was performed with 10 L/min sampling flow rate and at the 12 V/50 mA charging condition and 7 kV collection voltage. The data are averages and standard deviations from 3 repeats.

DETAILED DESCRIPTION OF THE INVENTION

A device based on the proposed method comprises two electrodes, one of which is grounded while the other is connected to high voltage having a sign opposite to the sign of electrical charge of the incoming particles. The electrode connected to the high voltage (also called collection electrode) is covered by a superhydrophobic substance. The width of this electrode is approximately equal to the diameter of a droplet that will be used to collect the particles deposited on the electrode. If the voltage connections are reversed (the electrode with superhydrophobic surface is grounded and the other is connected to high voltage), then the high voltage sign should be the same as the sign of electrical charge on the incoming particles. The electrical charge to the particles is provided by a separate ionizing/charging module (not claimed in this application). The entire sampler is positioned at a 10 degree inclination angle to the horizontal. The charged airborne particles are drawn into the sampler by a pump or an air mover and then are deposited onto the collection electrode by the action of the electrostatic field. At the end of the sampling period a liquid droplet is injected at the top of the sampling chamber onto the surface of the collection electrode and the droplet rolls-off of electrode's surface under the force of gravity removing the deposited particles. The droplet containing particles is then capture by a container or container system for subsequent analysis.

One potential embodiment of the new sampling method—an electrostatic precipitator with superhydrophobic surface (EPSS)—is shown in FIGS. 1A through 1D. FIG. 1A shows the overall view of the device, FIG. 1B presents more detail of the bottom plate housing the electrode with superhydrophobic surface, FIG. 1C shows the schematic of the front view of the device in detail, while FIG. 1D shows the side view of the device.

FIG. 1A shows an overall view of a particular embodiment of the device that has a shape of a closed half cylinder and consists of two detachable components: the top round part having a shape of a half cylinder and a bottom flat plate which closes the top part along the air flow axis. The top round part consists of a nonconductive housing 1 on the outside and a round conductive metal plate 2 on the inside. The metal plate 2 is grounded and is air-tightly affixed to the bottom of the non-conductive housing 1. The ground connection is provided via connector 3 penetrating the housing 1 and in firm contact with electrode 2. The bottom part consists of a non-conductive plate 4 housing the collection electrode 5 and two metal inlays 6. The collection electrode 5 is positioned in the middle of the bottom plate 4 and is opposite the apex of the ground electrode 2. The collection electrode 5 is positioned slightly below the surface of bottom plate 4 so that a groove of about 0.5-0.8 mm is formed. The collection electrode 5 is connected to the high voltage power source through connector 9. Most of the surface of the bottom plate 4 is covered by two conductive inlays 6 running parallel the air flow direction. The inlays 6 are flush with the surface of the plate 4 and are neither in contact with electrode 5 nor ground electrode 2. Presence of conductive surface on the bottom plate minimizes losses of charged particles to the non-conductive parts of the sampler. The collection droplet 8 is shown on the electrode 5 and at the end of the collection chamber.

FIG. 1B shows the bottom plate in more detail. The electrode 5 has a width of 2-3.5 mm. The width of the collection electrode could be different, but should be approximately equal to the diameter of the droplet 8 that will be used to remove the collected particles. The length of the sampling chamber is 254 mm, but different dimension could be used as long as it ensures efficient particle collection. The collection droplet 8 is shown on the electrode 5 and at the top of the collection chamber. Once the droplet 8 rolls down under the force of gravity picking up the particles deposited on the collection electrode 5 it will be captured by liquid capture system 13 positioned at the end of the collection chamber.

Figure 1B:
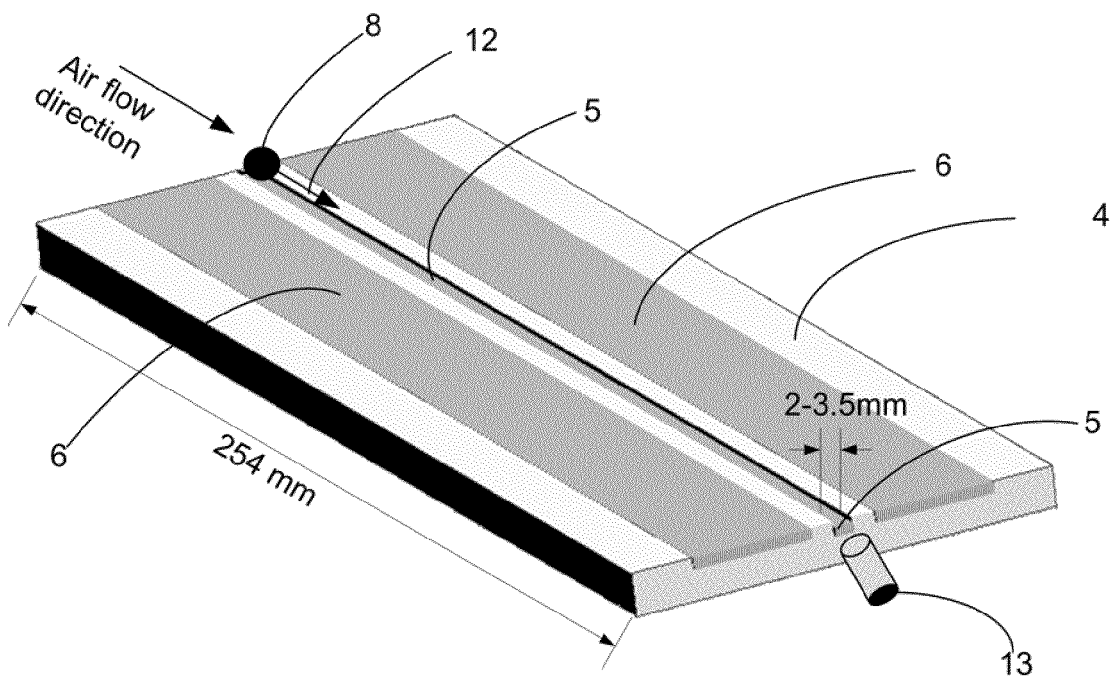
Figure 1C:
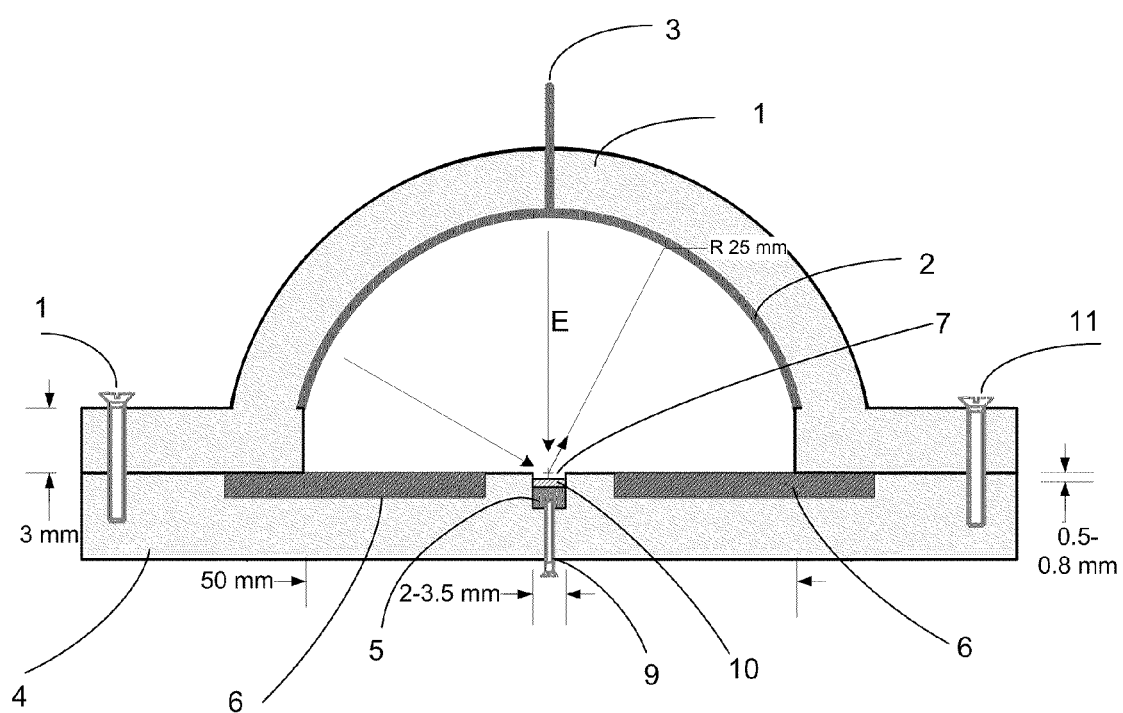

FIG. 1C shows the schematic of the front view of the device in more detail. The radius of the ground electrode 2 in this embodiment is ~25 mm, but a different radius could be used provided the voltage applied between the ground electrode 2 and the collection electrode 5 is strong enough to ensure deposition of charged particles onto collection electrode 5 covered with superhydrophobic substance 10. There are several commercially-available superhydrophobic substances that could be used. One particular typed was used when reducing this invention to practice and its details are provided in the "Experimental verification" section. The width of the flow channel depends on the radius of electrode 2 and for this embodiment is ~50 mm. The collection electrode 5 is positioned in the middle of the bottom plate 4 and is opposite the apex of ground electrode 2. The collection electrode 5 is positioned slightly below the surface of bottom plate 4 so that a groove 7 of about 0.5-0.8 mm would form. The groove ensures that when the collection droplet rolls down it stays on the top of the collection electrode 5 with superhydrophobic surface 10. Once the voltage across electrodes 2 and 5 is applied, the electrostatic field E is formed and focuses the particles toward the electrode 5. In this particular embodiment, the voltage of −7,000 V was used. The two halves of the sampler are air-tightly held by a number of screws 11 along the outer edges of the bottom part 4 and top part 1. Due to the presence of screws 11, the apparatus can be opened for cleaning, inspection or for the replacement of ground electrode 5. The thickness of the nonconductive parts of the collector is approximately 3 mm.

Figure 1D:
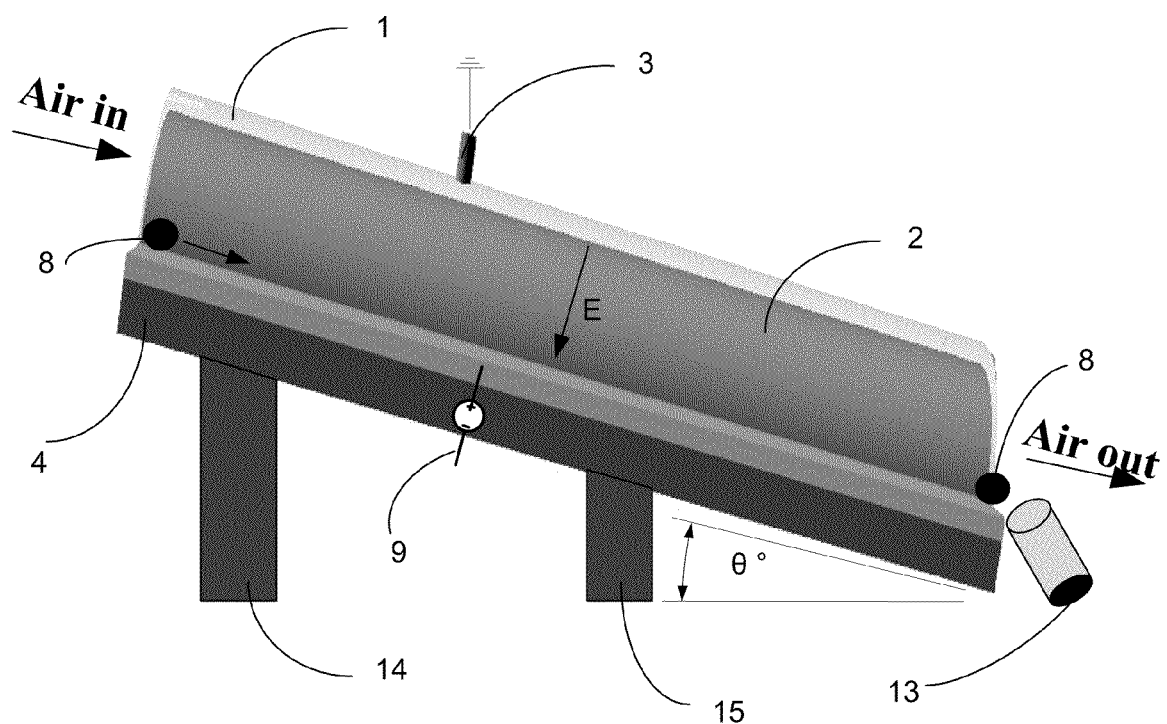

The side view of the collector is shown in FIG. 1D. The collector positioned at an angle θ to the horizontal (<10°). The support for the device provided by support columns 14 and 15 of uneven height which positions the device at an angle θ. At the end of sampling period a collecting droplet 8 is inserted at the inlet of the collector and once it rolls down is captured by the liquid capture system 13. The figure also shows the direction of electrostatic field E.

During the operation of the device, the air with particles is drawn by an external pump (not shown in FIGS. 1A-1D) so that air would move into the inlet of the EPSS. The airborne particles (biological and non-biological) are imparted an external electrical charge by a charger or an ionizer. The details of the pump and the charger as well as their placement relative to the collection chamber are discussed later. The charged particles enter the EPSS whereby the action of the electrostatic field E are deposited on the collection electrode 5, which is narrow and covered with superhydrophobic coating 10. Since the ground electrode 2 "engulfs" the electrode 5, the electrostatic field lines focus toward the electrode 5 pushing the particles toward it due to electrostatic forces. Once the sampling is complete, a droplet 8 is injected at the chamber's inlet onto the surface of the electrode 5 covered by superhydrophobic substance and rolls down under the force of gravity (direction arrow 12 in FIG. 1B) picking up the deposited particles. The groove 7 provides a guided path for the droplet. The droplet 8 containing collected particles is captured by a liquid capture system 13 positioned at the end of the collection chamber. The liquid capture system 13 could be either a single vial of carousel of vials or any other arrangement allowing securely capturing the droplet and transferring it or making it available for subsequent analysis. The droplet 8 available in the system 13 is then transferred to an analysis device(s) to be examined using different techniques.

Figure 2:
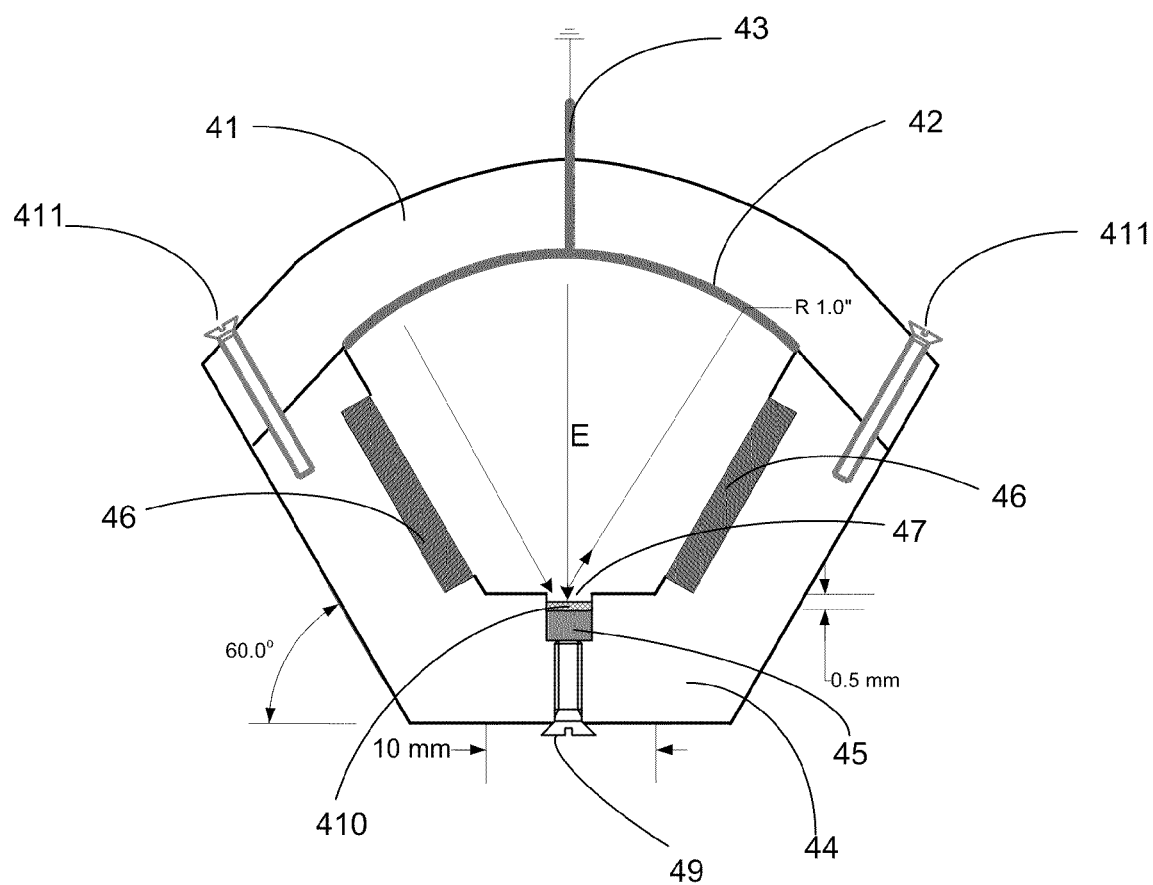

FIG. 2 presents a front view of a different embodiment of the electrostatic collection with superhydrophobic surface (EPSS). Here, instead of the half cylinder design, an inverted triangle design is used. The device consists of two detachable components: the upper part consisting of a nonconductive housing 41 on the outside and a conductive metal plate 42 having a shape of an arc on its inside. The metal plate 42 serves as an electrode which is grounded and is air-tightly affixed to the bottom of the nonconductive housing 41. The grounding connection is provided via connector 43 penetrating the shell 41 and in firm contact with the electrode 42. The radius of the ground electrode 42 in this embodiment is ~25 mm, but a different radius could be used provided the applied voltage ensures deposition of charged particles onto collection electrode 45. The shape of the lower part resembles letter "V", except that its bottom portion is flat and has a width of 10 mm. The collection electrode 45 is positioned in the apex of the triangle and in the middle of the bottom part 44 opposite the apex of electrode 42. The collection electrode 45 is slightly below the surface of bottom plate 44 so that a groove of about approximately 0.5 mm is formed (item 47 on FIG. 2) for improved guidance of the injected droplet. The electrical contact to the collection electrode 45 is provided by a connector 49 connected to the high voltage power. The side walls of the lower part (letter V) are at 60° to the horizontal and most of their surface is covered by two conductive inlays 46 running parallel to the air flow direction. The inlays 46 are flush with the surface of the walls and are neither in contact with electrode 45 nor ground electrode 42. Presence of conductive surface on the walls minimizes losses of charged particles to the non-conductive parts of the sampler. The ground electrode 45 has a width of 2-3.5 mm and is covered with the superhydrophobic coating 410. The coating is applied prior to sampling. As in the previous embodiment, the width of the collection electrode should be approximately equal to the diameter of the droplet that will be used to remove the collected particles. The two detachable components of the sampler are held together by screws 411. If needed, the screws can be removed and the apparatus can be opened for cleaning, inspection or for the replacement of collection electrode 45. Lengthwise, the collector is positioned at approximately 10 degree angle to the horizontal similar to the embodiment in FIG. 1D. The particular embodiment presented in FIG. 2 streamlines electrical field lines E which would ensure even more efficient collection of the particles.

Figure 3:
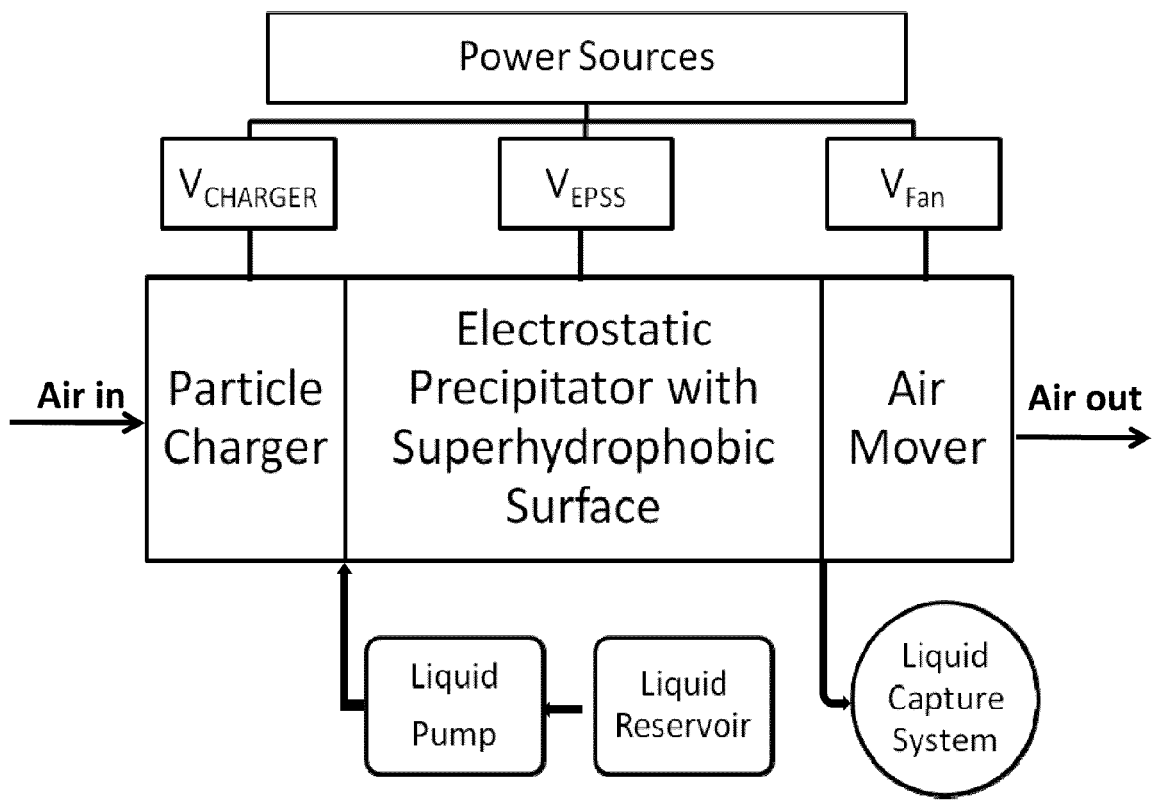

FIG. 3 presents a block diagram of the sampling system incorporating electrostatic collector with superhydrophobic surface (EPSS). A particle charger is air-tightly connected to the front of the EPSS and an air mover (pump or similar) is air-tightly connected to the back of the EPSS. The air mover provides an air flow through the system at a predetermined flow rate for a predetermined time. The reduction to practice of the EPSS having a shape of half-cylinder (FIGS. 1A-1D) was tested at 10 L/min, but much higher flow rates could be used depending on the efficiency of the particle charger and capacity of the air mover. The particle charger could be one of many commercially available ionizing or charging devices. The reduction to practice of the EPSS having a shape of half-cylinder (FIGS. 1A-1D) was tested with an AS 150 ionizer (Wein Products Inc., Los Angeles, Calif.) which imparted positive charge. During the operation of the EPSS collector, the air mover draws the particles into the charger, where they acquire an electrical charge and then are deposited on the collection electrode covered with a superhydrophobic substance inside the EPSS as described above. Any substance that renders the electrode's surface superhydrophobic with water contact angle above 150° could be used to cover the collection electrode. The reduction to practice of the EPSS having a shape of half-cylinder was tested with HIREC-1450 (NTT Corporation Inc., Japan). Once the collection is complete, a liquid pump draws the collection liquid from the reservoir and injects a liquid droplet (5-60 μL) at the top of the EPSS onto the collection electrode. Since the EPSS is positioned at a 10° angle to the horizontal (as shown in FIG. 1D), the droplet rolls down under the force of gravity picking up the deposited particles and is then captured by a liquid capture system (item 13 in FIGS. 1B and 1D). The size of the droplet is controlled by adjusting the diameter of the liquid pump's injection needle and its operating time. The droplet needs to be applied only once after the entire sampling period which allows for very efficient concentration of collected particles. The voltage to the charger, $V_{CHARGER}$, high voltage to the EPSS, $V_{EPSS}$, and voltage to the air mover, $V_{FAN}$, are provided by various power sources connected to the sampling system. The high voltage $V_{EPSS}$ should be in the range of 5,000-10,000 V for the embodiment presented here.

EXPERIMENTAL VERIFICATION OF THE INVENTION

Figure 4:
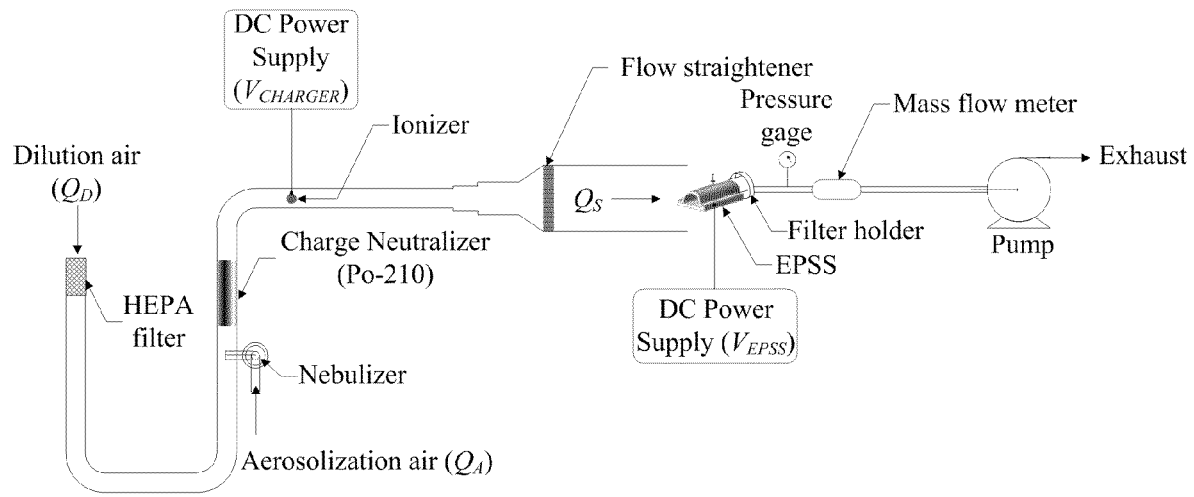

FIG. 4 shows the experimental set-up that was used to test the performance of the electrostatic precipitator with superhydrophobic surface (EPSS) described in this invention. The ability of the new method to collect particles into a small droplet via a combination of electrostatic field and an electrode with superhydrophobic surface allows achieving very high concentration rates. The results presented below show that the concentration rates of the EPSS can exceed $1 \times 10^6$/min, which is much higher than achieved by electrostatic samplers described in prior art.

The entire experimental setup shown in FIG. 4 was housed inside a Class II Biosafety cabinet (NUAIRE Inc., Plymouth, Minn.) so that airborne particles not collected by the device are properly eliminated. A Collison nebulizer (BGI Inc., Waltham, Mass.) was used to aerosolize the green fluorescent polystyrene latex (PSL) particles (Duke Scientific, Palo Alto, Calif.) from a liquid suspension at a flow rate, $Q_A$ (4 L/min) and the test aerosol was dried and diluted with HEPA-filtered air flow, $Q_D$ (36 L/min). The 40 L/min aerosol stream was passed through a 2-mCi Po-210 charge neutralizer to reduce aerosolization-related particle charges to Boltzmann equilibrium. The electrically neutralized particles then passed through a 0.035 m duct housing a vertically oriented ionizer (AS 150, Wein Products Inc., Los Angeles, Calif.) which imparted positive charge on the particles under controlled voltage and current settings. The electrically charged aerosol passed through a flow straightener and entered the testing chamber where it was collected by the EPSS at a flow rate $Q_s$. A 47 mm glass fiber after-filter (Type A/E, Pall Inc., East Hills, N.Y.) was used to collect particles not deposited inside the EPSS, thereby allowing to determine the concentration of particles retained inside the EPSS. Performance of the EPSS was tested at 3 collection flow rates, $Q_s$=2, 5, and 10 L/min, which were provided by an external pump and monitored using a mass flow meter (TSI Inc., Shoreview, Minn.). The tests were performed with green fluorescent polystyrene latex (PSL) particles (Duke Scientific, Palo Alto, Calif.) of 0.5, 1.2, 1.9, 3.2 and 5.1 μm in aerodynamic diameter ($d_a$) and the collected particles were removed by water droplets of 5, 10, 20, 40, and 60 μL. Another series of tests was performed with airborne bacteria and water droplets of 5 and 40 μL. The collection electrode was coated with superhydrophobic spray HIREC-1450 (NTT Corporation Inc., Japan) and left to dry at 60° C. for at least 1 hour. The coating procedure was repeated twice to achieve a uniform coating. One stable DC power supply (BK Precision, Yorba Linda, Calif.) provided power to the ionizer (12V/50 mA), while another stable DC high voltage power supply (Bertan Associates, Inc, Valhalla, N.Y.) provided negative voltage (−7 kV) to the precipitator to collect positively charged particles.

The mass concentration of fluorescent PSL particles removed by a droplet, collected by the after-filter, as well as the concentration of particles deposited on the ground electrode and elsewhere inside the sampler were quantified using a fluorometer (Sequoia-Turner Corp., Mountain View, Calif.). The ability of the rolling droplets to collect deposited on the collection electrode was tested by consecutively injecting three droplets and by comparing particle concentration in each droplet with concentration of particles deposited on the collection electrode. Here, each sequential hydrosol sample ($1^{st}$, $2^{nd}$ and $3^{rd}$ water droplets) collected in separate vials was evaporated using a heat gun (Master-Carr, Inc., Robbinsville, N.J.) and then 4 mL ethyl acetate (EMD Chemicals Inc, Gibbstown, N.J.) was added to the vial and set aside for 20 minutes to dissolve the PSL particles. An after-filter containing particles that escaped the EPSS was soaked in 25 mL of ethyl acetate in a glass container for 4 hours to elute the fluorescein dye from the PSL particles. The mass of PSL particles remaining on the collection electrode (not removed by three rolling droplets) as well as the mass of PSL particles deposited on other components of the collector was quantified by extracting them using a defined quantity of ethyl acetate and analyzing using a fluorometer. The concentration of aerosolized PSL particles was such as to ensure that fluorometer reading of each sample was approximately ten-fold of the background fluorescence of ethyl acetate and the measurements were adjusted for background readings. In addition, the concentrations of all analyzed samples were within the linearity range of the fluorometer. A fraction of particles deposited in any individual part of the system (water droplet (s), collection electrode, ground electrode, bottom plate, or after-filter), $\eta_i$, can be defined as a ratio of the relative concentration of particles in the individual part, $C_i$, to the total relative concentration of the aerosol entering the sampler, $C_{TOTAL}$, and can be expressed according to Eq. 2:

$$\eta_i = \frac{C_i}{C_{TOTAL}} = \frac{C_i}{\sum_i C_i} \quad (2a)$$

$$C_i = \frac{I_i \cdot v_i}{Q_S \cdot t}, \quad (2b)$$

where, $I_i$=concentration of fluorescein eluded in ethyl acetate (fluorometer reading) for a component i; $v_i$=volume of solution used to elute the tracer for a component i; $Q_S$=air sampling flow rate; and, t=sampling time. The $C_{TOTAL}$ is the sum of aerosol particle concentrations in all individual parts of the sampler. For all testing conditions the sampling was isoaxial and isokinetic or near-isokinetic and $C_{TOTAL}$ was found to agree with particle concentration in the test chamber (upstream of the sampler) within 4%. By using Eq. 2 we determined the efficiency with which the droplets remove the particles deposited on the collection electrode as well as the sampler's collection efficiency based on the particle concentration in the water droplets ($C_{WD(5)}/C_{TOTAL}$). We also determined concentration rate, $R_C$ (Eq. 1).

Figure 5:
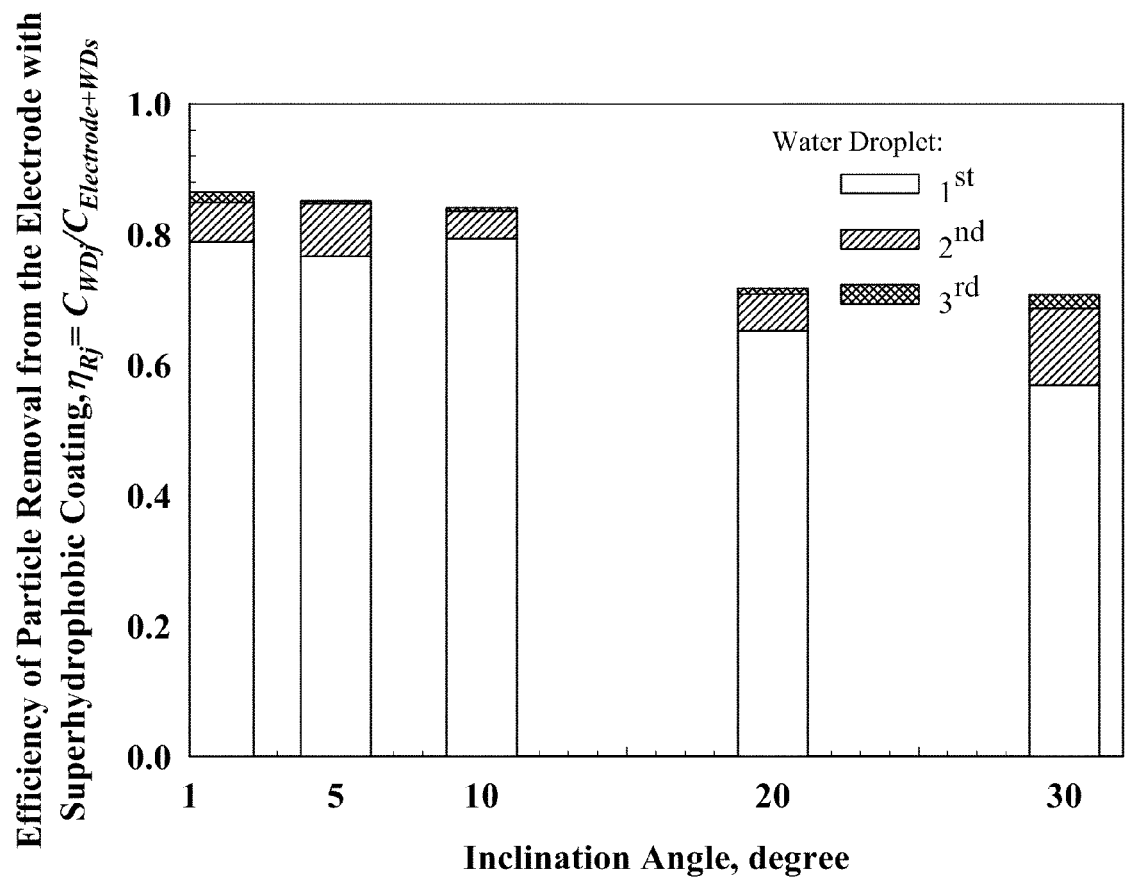

The data presented in FIG. 5 show the efficiency ($\eta_{R_j}$) with which 3.2 μm PSL particles deposited on the electrode with superhydrophobic surface are removed by three 40 μL it sequential droplets ($1^{st}$, $2^{nd}$, and $3^{rd}$) as a function of the inclination angle (1, 5, 10, 20, and 30 degrees) at 10 L/min sampling flow rate. It can clearly be seen that the vast majority of deposited particles is removed by the first droplet. The same pattern was also observed for other particle and droplet sizes. FIG. 5 also indicates that for maximum particle removal efficiency the inclination angle should be less than 10 degrees.

Figure 6:
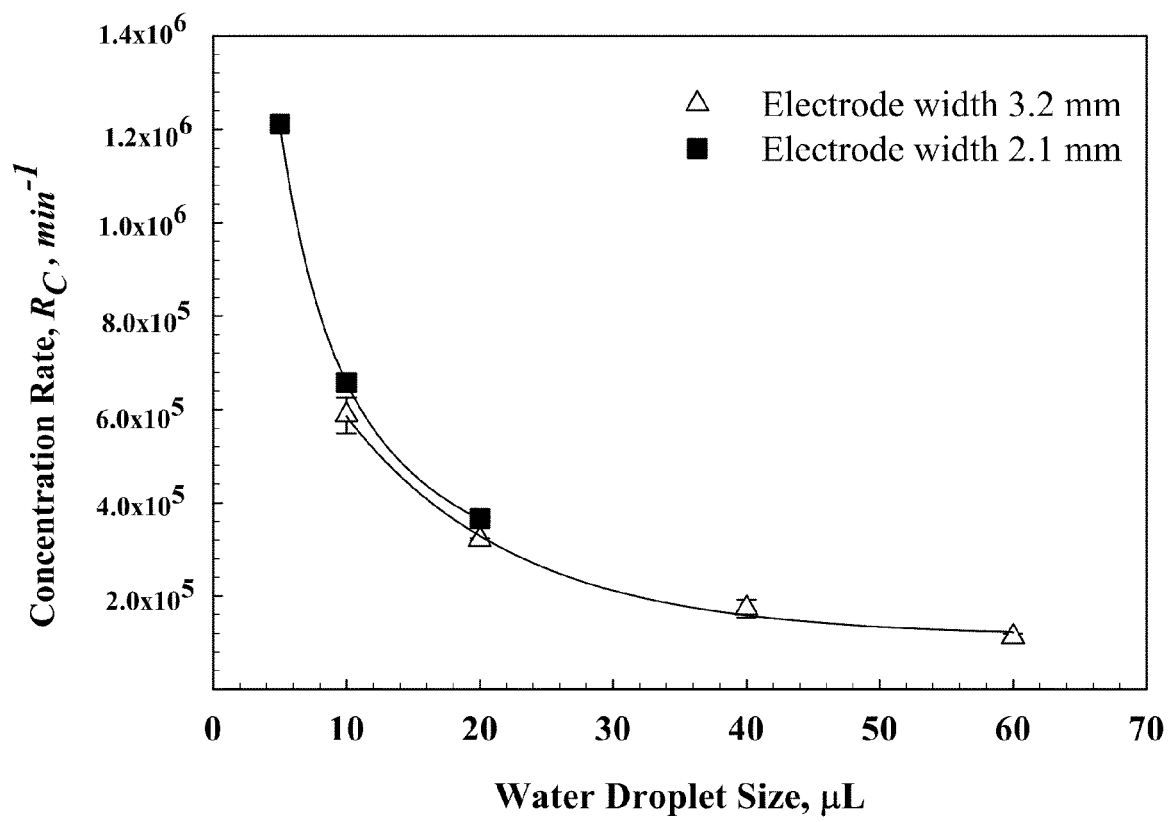

Concentration rates for 3.2 μm PSL particles with two electrode widths and different volumes of collecting droplet are shown in FIG. 6. The sampling was performed at 10 L/min flow rate and the concentration rates are based on one and only droplet inserted at the top of the sampling chamber. The concentration rate $R_C$ for 10 μL was ~$6 \times 10^5$/min. When the width of the collection electrode was reduced from 3.2 mm to 2.1 mm and collecting droplet of 5 μL was used, the EPSS sampler achieved the concentration rate of $1.2 \times 10^6$/min.

Figure 7:
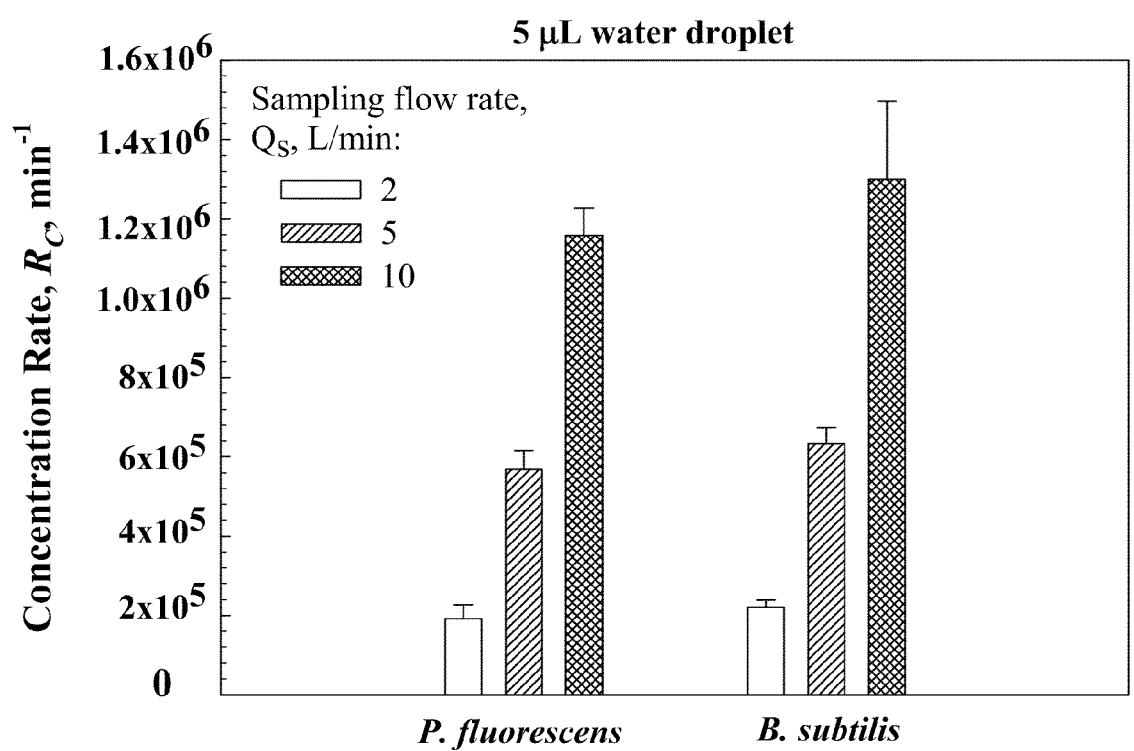

FIG. 7 presents the concentration rates of the EPSS when collecting the airborne bacteria *Pseudomonas fluorescens* and *Bacillus subtilis* at different sampling flow rates. The collected bacteria were removed with 5 μL water droplet (one droplet only). Both test microorganisms are representatives of genera and species typically found in ambient air environments (Nevalainen, 1989; Gorny and Dutkiewicz, 1998), and representatives of the aerodynamic diameters of target biological agents (Macher, 1997). Their preparation for testing is described elsewhere (Yao and Mainelis, 2006a). The concentration of bacteria collected by the water droplet was determined using epifluorescence microscopy as described elsewhere (Mainelis et al., 2002b). The reference concentration was determined by isokinetically sampling the same microorganisms in the test chamber on a filter, extracting them from the filter using the procedures described elsewhere (Wang, 2001) and counting them under a microscope. As shown in FIG. 7, the concentration rate of the sampling technology presented in this patent application exceeds $1.2 \times 10^6$/min when sampling airborne bacteria *Pseudomonas fluorescens* and *Bacillus subtilis*. Such high concentration rates are not achieved with any other currently existing samplers for airborne biological agents. The concentration rates exceeding $1.2 \times 10^6$/min clearly indicate the advantage of the described technology over prior art in the area of air sampling. The tests described above were performed with 10 min sampling times. Much longer sampling times can be used as well and the particles collected during the entire sampling period are accumulated in one collection droplet.

Figure 8:
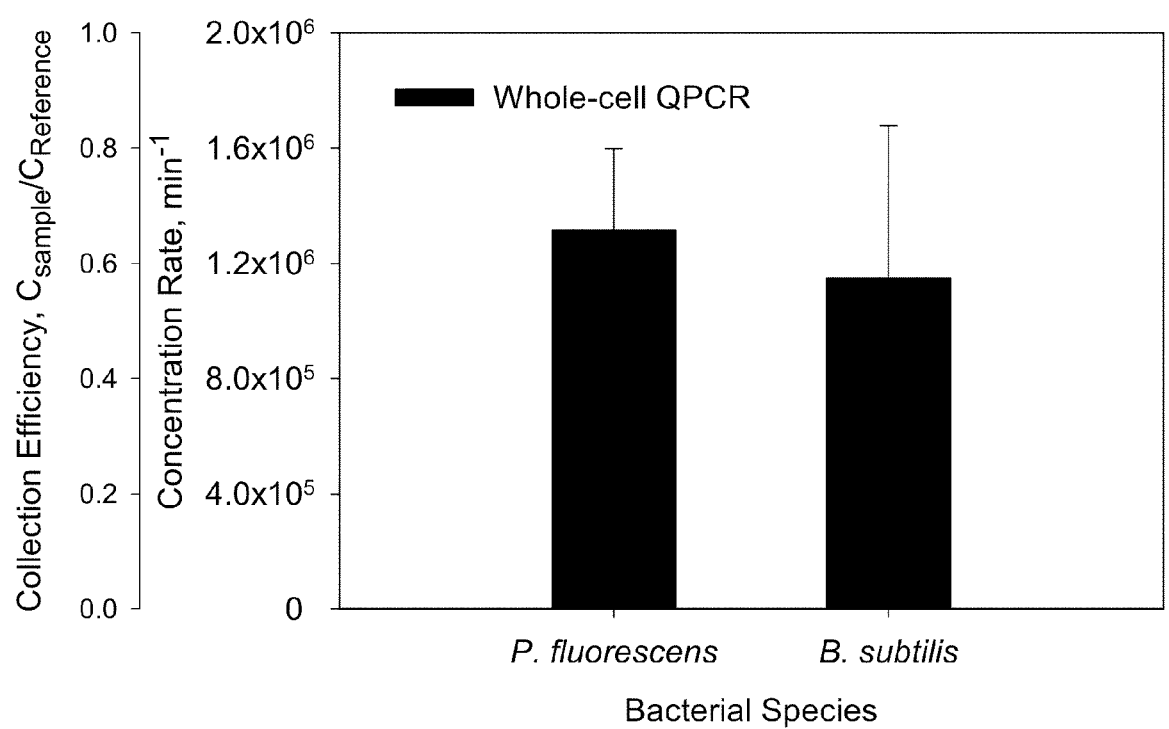

Since the biological particles are collected into liquid they could be analyzed by numerous methods, including analysis by molecular tools such as polymerase chain reaction (PCR). FIG. 8 shows the collection efficiency and the resulting concentration rate of the EPSS when the bacteria collected by the sampler were analyzed using whole-cell quantitative real time polymerase chain reaction (QPCR). In the whole-cell QPCR method, the bacteria in the entire sample are analyzed by the QPCR directly without extracting the genomic DNA first. The result from the reaction is entered into standard (calibration) curves to determine the cell quantity. The details of the method are described elsewhere (An et al., 2006; An et al., 2009). The sampling was performed at 10 L/min sampling flow rate and the collected bacteria were removed by one 5 μL droplet. The reference concentration was determined by isokinetically sampling the same bacteria on filter, extracting them and analyzing using QPCR. The data in FIG. 8 show that the collection efficiency of the EPSS was ~60% for both bacteria and the resulting concentration rate was $1.2 \times 10^6$/min or higher. These results demonstrate the compatibility of the sampling method described in this application with the PCR techniques. In addition, it demonstrates that the sample volume could be analyzed in its entirety without loosing the collected particles. Loss of sample is common in current sampling technologies due to large volumes of the collection liquid and inability to process the entire sample. The approach demonstrated in this patent application concentrates the airborne particles into very small amounts of liquid and, as a consequence, will allow detecting low concentrations of airborne biological and non-biological-agents.

REFERENCES

An, H. R., Mainelis, G., and White, L. (2006). Development and Calibration of Real-time PCR for Quantification of Airborne Microorganisms in Air Samples. *Atmospheric Environment* 40: 7924-7939.

An, H. R. A., Han, I.-K. H., White, L., and Mainelis, G. (2009). Quantitative Real-Time PCR for Bioaerosol Detection: Analysis of Factors Affecting Standard Curves *Environmental Science and Technology*: Submitted Barthlott, W., and Neinhuis, C. (1997). Purity of the sacred lotus, or escape from contamination in biological surfaces. *Planta* 202(1): 1-8.

Carlson, C., DeGange, J., Cable-Dunlap, P., Halverson, J. (2004). Aerosol-to-Liquid Particle Extraction System (ALPES). *Abstracts of 2nd Joint Conference on Point Detection for Chemical and Biological Defense*, Williamsburg, Va., 1-5 Mar. 2004.

Carlson, C., DeGange, J., Cable-Dunlap, P., Halverson, J. (2005). Portable Liquid Collection Electrostatic Precipitator. USPTO. USA, Westinghouse Savanna River Co., LLC. U.S. Pat. No. 6,955,075 B2: 9.

Douwes, J., Thorne, P., Pearce, N., and Heederik, D. (2003). Bioaerosol Health Effects and Exposure Assessment: Progress and Prospects. *Annals of Occupational Hygiene* 47(3): 187-200.

Gorny, R. L., and Dutkiewicz, J. (1998). Evaluation of Microorganisms and Endotoxin Levels of Indoor Air in Living Rooms Occupied by Cigarette Smokers and Non-Smokers in Sosnowiec, Upper Silesia, Poland. *Aerobiologia* 14: 235-239.

Haglund, J. S. (2003). Two linear slot nozzle virtual impactors for concentration of bioaerosols. *Department of Mechanical Engineering, Texas A&M University*. College Station, Tex. Ph.D. Dissertation.

Hindson, B. J., Brown, S. B., Marshall, G. D., McBride, M. T., Makarewicz, A. J., Gutierrez, D. M., Wolcott, D. K., Metz, T. It, Madabhushi, R S., Dzenitis, J. M., and Colston, B. W., Jr. (2004). Development of an Automated Sample Preparation Module for Environmental Monitoring of Biowarfare Agents. *Anal. Chem.* 76: 3492-3497.

Hindson, B. J., Makarewicz, A. J., Setlur, U.S., Henderer, B. D., McBride, M. T., and Dzenitis, J. M. (2005a). APDS: the autonomous pathogen detection System. *Biosensors and Bioelectronics* 20(10): 1925-1931.

Hindson, B. J., McBride, M. T., Makarewicz, A. J., Henderer, B. D., Setlur, U.S., Smith, S. M., Gutierrez, D. M., Metz, T. R., Nasarabadi, S. L., Venkateswaran, K. S., Farrow, S. W., Colston, B. W., and Dzenitis, J. M. (2005b). Autonomous Detection of Aerosolized Biological Agents by Multiplexed Immunoassay with Polymerase Chain Reaction Confirmation. 77: 284-289.

Lu, C., and Hungsung, H. (1998). A sectional model to predict performance of a plate-wire electrostatic precipitator for collecting polydisperse particles. *J. Aerosol Sci.* 29: 295-308.

Ma, M., and Hill, R. M. (2006). Superhydrophobic surfaces. *Current Opinion in Colloid & Interface Science* 11: 193-202.

Macher, J. M. (1997). Evaluation of Bioaerosol Sampler Performance. *Appl. Occup. Environ. Hyg.* 12(11): 730-736.

Mainelis, G., Adhikari, A., Willeke, K., Lee, S.-A., Reponen, T., and Grinshpun, S. A. (2002a). Collection of airborne microorganisms by a new electrostatic precipitator. *Journal of Aerosol Science* 33(10): 1417-1432.

Mainelis, G., Górny, R. L., Reponen, T., Trunov, M., Grinshpun, S. A., Yadav, J., Baron, P. A., and Willeke, K. (2002b). Effect of Electrical Charges and Fields on Injury and Viability of Airborne Bacteria. *Biotech. Bioeng.* 79: 229-241.

Mainelis, G., Masquelier, D., Makarewicz, A., and Dzenitis, J. (2005). Performance characteristics of the aerosol collectors of the autonomous pathogen detection system (APDS). *Aerosol Science and Technology* 39(5): 461-471.

Mainelis, G., Willeke, K., Adhikari, A., Reponen, T., and Grinshpun, S. A. (2002c). Design and collection efficiency of a new electrostatic precipitator for bioaerosol collection. *Aerosol Science and Technology* 36(11): 1073-1085.

Mainelis, G., Willeke, K., Baron, P., Grinshpun, S. A., Reponen, T., Górny, R. L., and Trakumas, S. (2001). Electrical Charges on Airborne Microorganisms. *Journal of Aerosol Science* 32: 1087-1110.

McBride, M. T., Masquelier, D., Hindson, B. J., Makarewicz, A. J., Brown, S., Burris, K., Metz, T., Langlois, R. G., Tsang, K. W., Bryan, R., Anderson, D. A., Venkateswaran, K. S., Milanovich, F. P., and Colston, B. W. (2003). Autonomous detection of aerosolized *Bacillus anthracis* and *Yersinia pestis*. *Anal. Chem.* 75(20): 5293-5299.

Monn, C. (2001). Exposure assessment of air pollutants: a review on spatial heterogeneity and indoor/outdoor/personal exposure to suspended particulate matter, nitrogen dioxide and ozone. *Atmospheric Environment* 35(1): 1-32.

Nevalainen, A. (1989). *Bacterial Aerosols in Indoor Air*. Ph.D. Dissertation. Kuopio, Finland, National Public Health Institute.

Pant, K., Wang, G., Feng, J., and Sundaram, S. (2008). Electrostatic Sampler and Method. USPTO. US, CFD Research Corporation. U.S. Pat. No. 7,428,848 B2: 16.

Rose, H. E., and Wood, A. J. (1956). *An introduction to electrostatic precipitator in theory and practice*. London, Constable and Company.

Seo, Y. (2007). Design of Wetted Wall Bioaerosol Concentration Cyclone. *Dept of Mech Eng. College Station, Texas A&M University*. Ph.D. Dissertation.

Wang, Z., Reponen, T., Grinshpun, S. A., Górny, R. L., and Willeke, K. (2001). Effect of Sampling Time and Air Humidity on the Bioefficiency of Filter Samplers for Bioaerosol Collection. *J. Aerosol Sci.* 32: 661-674.

WHO (1990). Indoor Air Quality: Biological Contaminants. *Report on a World Health Organization Meeting*. Rautavaara, Finland, Aug. 29-Sep. 2, 1988.

Womiloju, T. O., Miller, J. D., Mayer, P. M., and Brook, J. R. (2003). Methods to determine the biological composition of particulate matter collected from outdoor air. *Atmospheric Environment* 37(31): 4335-4344.

Yao, M., and Mainelis, G. (2006a). Effect of Physical and Biological Parameters on Enumeration of Bioaerosols by Portable Microbial Impactors. *Journal of Aerosol Science* 37(11): 1467-1483.

Yao, M., and Mainelis, G. (2006b). Utilization of natural electrical charges on airborne microorganisms for their collection by electrostatic means. *Journal of Aerosol Science* 37(4): 513-527.

Yao, M., Mainelis, G., and An, H. It (2005). Inactivation of microorganisms using electrostatic fields. *Environmental Science & Technology* 39(9): 3338-3344.

Zaromb, S., and Martell, D. J. (2007). Aerosol Collection Apparatus and Methods. USPTO. U.S. application Ser. No. 11/473,748: 18.

Zhuang, Y., Kim, Y. J., Lee, T. G., and Biswas, P. (2000). Experimental and theoretical studies of ultrafine particle behavior in electrostatic precipitators. *J. Electrostatics* 48: 245-260.

What I claim as my invention is:

1. A method for collecting electrically charged airborne particles of biological and non-biological origin and concentrating them in small amounts of liquid, the method comprising a device having:

at least one air flow channel assembly comprising a first electrode and a second electrode, the first electrode disposed substantially parallel to the second electrode and wherein both said electrodes are parallel to the direction of air flow through the channel assembly and whereby said air flow channel has an inlet and an outlet;

whereby one of the electrodes of said assembly is connected to high voltage, while the other is grounded to effect creation of an electrostatic field in said air flow channel;

whereby one of said electrodes is narrower than the other electrode to effect the focusing of the electrostatic field toward the narrower electrode once the voltage is applied;

whereby the narrower electrode is covered with a superhydrophobic substance to ensure high contact angle for liquids placed on its surface;

whereby the entire flow channel is positioned at an angle to the horizontal;

whereby the electrically charged airborne particles pulled through said air flow channel are deposited onto the narrower electrode with the superhydrophobic surface under the action of the electrostatic field;

whereby a small liquid droplet placed near the air inlet of the air flow channel and on top of the electrode covered by a superhydrophobic coating rolls down under the force of gravity and picks up the particles that have been deposited onto said electrode with superhydrophobic coating;

whereby the droplet that has collected particles deposited on the electrode with the superhydrophobic coating is captured into a container positioned near the outlet of the air flow channel; and whereby said droplet and particles contained wherein are analyzed by a variety of methods to determine the presence of biological and non-biological particles.

2. The method of claim 1, wherein the device further comprises:

an electrostatic collection module comprising:

an air flow channel assembly having a shape of a closed half cylinder, wherein one of the electrodes has a shape of half cylinder;

the second electrode positioned in a plate enclosing the first electrode in the direction of air flow; and whereby the second electrode is narrower than the first electrode; and whereby the second electrode is positioned opposite the first electrode; and whereby the second electrode is slightly below the surface of a plane it is positioned in to form a groove; and whereby the second electrode is covered with a superhydrophobic substance; and whereby a voltage is applied across the two electrodes;

a charger to electrically charge airborne particles, whereby said charger is positioned at the inlet of the electrostatic collection module to electrically charge the airborne particles being drawn into the module; and an air mover for drawing airborne particles into the electrical charger, through the electrostatic collection module, and out through the outlet and whereby the air mover is positioned at the end of the electrostatic collection module; and one or more power sources operatively connected to the particle charger, the electrostatic collection module, and to the air mover; and a liquid pump, whereby said pump injects the droplets of various sizes and at various time intervals at the top of the air flow channel and into the groove containing the second electrode; and a liquid capture system positioned between the electrostatic collection module and the air mover to capture the liquid droplet(s) injected at the top of the electrostatic collection module whereby said droplet(s) have accumulated particles that have been deposited onto the electrode coated with superhydrophobic substance.

3. The method of claim 1, wherein the device further comprises liquid droplets of volume less than 100 μL being used to remove the particles deposited on the electrode covered with superhydrophobic substance.

4. The method of claim 1, wherein the device further comprises the width of the electrode with superhydrophobic coating being sized proportionately to the diameter of the collecting droplet to accommodate various sizes of the collecting droplet.

5. The method of claim 1, wherein the device further comprises the electrode not covered with superhydrophobic substance being grounded and where the electrode that is covered with superhydrophobic substance is connected to high voltage and whereby said voltage has a sign opposite the sign of electrical charge of particles being sampled.

6. The method of claim 1, wherein the device further comprises the electrode with superhydrophobic coating being grounded and high voltage being applied to the other electrode and whereby said high voltage has the same sign as the sign of electrical charge of particles being sampled.

7. The method of claim 1, wherein the device further comprises the air flow channel being positioned at an angle to the horizontal with the angle being such as to ensure the roll-off of the droplets is assisted only by the force of gravity.

8. The method of claim 1, wherein the device further comprises the air flow channel assembly having a shape resembling that of an inverted triangle with an apex facing downward; and one of the electrodes having a shape of an arc with its highest point facing upward; and the second electrode is positioned opposite the first electrode in the apex of the triangle; and the second electrode is narrower than the first electrode; and the second electrode is slightly below the surface of a plane it is positioned in; and the second electrode is covered with a superhydrophobic substance; and the side walls of the triangle are at 60 degrees to horizontal; and whereby most of the inside of said walls are covered by conducting inlays to minimize losses of charged particles.

* * * * *